United States Patent [19]

Kusch

[11] Patent Number: 5,740,227
[45] Date of Patent: Apr. 14, 1998

[54] X-RAY APPARATUS WITH A CEILING SUSPENSION

[75] Inventor: Jochen Kusch, Effeltrich, Germany

[73] Assignee: Siemens Aktiengesellschaft, Munich, Germany

[21] Appl. No.: 848,874

[22] Filed: May 1, 1997

[30] Foreign Application Priority Data

Jun. 10, 1996 [DE] Germany .................. 196 23 115.9

[51] Int. Cl.$^6$ .................................................. H05G 1/08
[52] U.S. Cl. ........................................... 378/91; 378/197
[58] Field of Search .............................. 378/91, 195–197

[56] References Cited

U.S. PATENT DOCUMENTS 4,679,223  7/1987  Ohlson et al. ......................... 378/197

OTHER PUBLICATIONS

"Handbuch der Industriellen Messtechnik," Profos et al., Eds. (1992), pp. 218–219.

*Primary Examiner*—Craig E. Church
*Attorney, Agent, or Firm*—Hill & Simpson

[57] ABSTRACT

X-ray apparatus with a ceiling suspension has a motor for displacing and positioning the X-ray apparatus and a motion control circuit which superimposes a dynamic motion factor on the motor output so that pendulum motions during an acceleration of the apparatus are counteracted. For this purpose, a filter is connected in the motion control circuit in front of the setting element of the motor, the filter being dimensioned so as to correspond to the characteristic system behavior, and compensates oscillations of the apparatus.

2 Claims, 2 Drawing Sheets

X-RAY APPARATUS WITH A CEILING SUSPENSION

BACKGROUND OF THE INVENTION

1. Field of the Invention

The present invention is directed to an X-ray apparatus from a ceiling mount.

2. Description of the Prior Art

In the use of an X-ray apparatus suspended from the ceiling, e.g. a C-arm apparatus, such as are used in angiography, the apparatus can be caused undesirably to oscillate in a pendulum fashion. This means that the operator must wait a certain time after each such motion, until the oscillation of the apparatus no longer has an effect on the X-ray image.

SUMMARY OF THE INVENTION

An object of the present invention is to provide an X-ray apparatus of the type suspended from the ceiling having a motion control circuit by means of which pendulum motion is largely avoided.

The above object is achieved in accordance with the principles of the present invention in an x-ray apparatus having a ceiling suspension with a motor for moving the apparatus along the ceiling, the apparatus producing pendulum-like oscillations when moved, and having a filter connected in front of a setting element for the motor. The filter electronically represents the characteristic oscillation behavior of the apparatus, and a motor control circuit includes stages for using this modeled behavior to produce a motion-compensating factor, which is electronically superimposed on the motor control signals, so that the motor output is compensated for the pendulum-like motion. The resulting behavior of the apparatus thus is devoid of the pendulum-like motion, so that an operator does not have to wait, after moving the apparatus, for the pendulum-like oscillations to subside.

DESCRIPTION OF THE PREFERRED EMBODIMENTS

Figure 1:
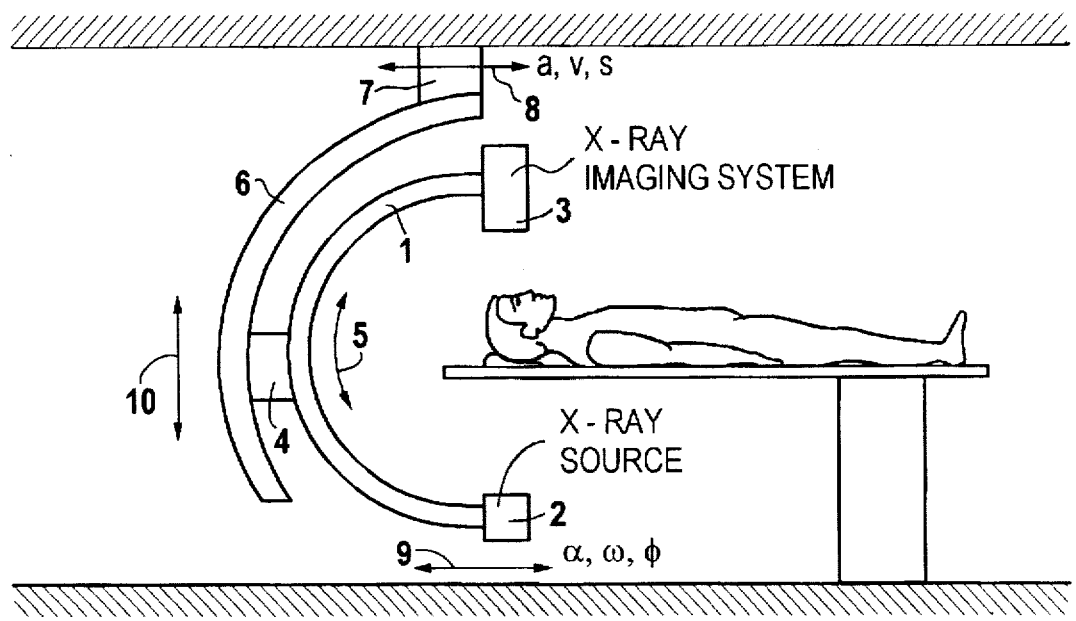
FIG. 1 shows an X-ray apparatus with a ceiling suspension, for the illustration of the basis of the invention.

The X-ray apparatus shown in FIG. 1 has a C-arm 1, at one end of which is mounted an X-ray source 2, and at the other end of which is mounted an imaging system 3. The C-arm 1 is displaceable in a mount 4 along its circumference, and can be rotated around a horizontal axis (double arrow 5). The mount 4 is displaceable along a bow 6, whereby the height position of the x-ray source 2 and the imaging system 3 can be set. The bow 6 is mounted on a ceiling suspension 7.

The double arrow 8 indicates the motion of the entire apparatus in the horizontal direction, including the acceleration a, the velocity v, and the path s of this motion. The double arrow 9 indicates the motion of the C-bend 1, including its acceleration a during rotation in the direction of the double arrow 5, its angular velocity $\omega$ and its angle of oscillation $\phi$. The double arrow 10 indicates the orbital excursion of the C-arm 1 during displacement of the mount 4 along the bow 6.

In the following, the problem of the pendulum motion of the apparatus and the avoidance thereof is explained for the example of longitudinal motion (double arrow 8).

Figure 2:
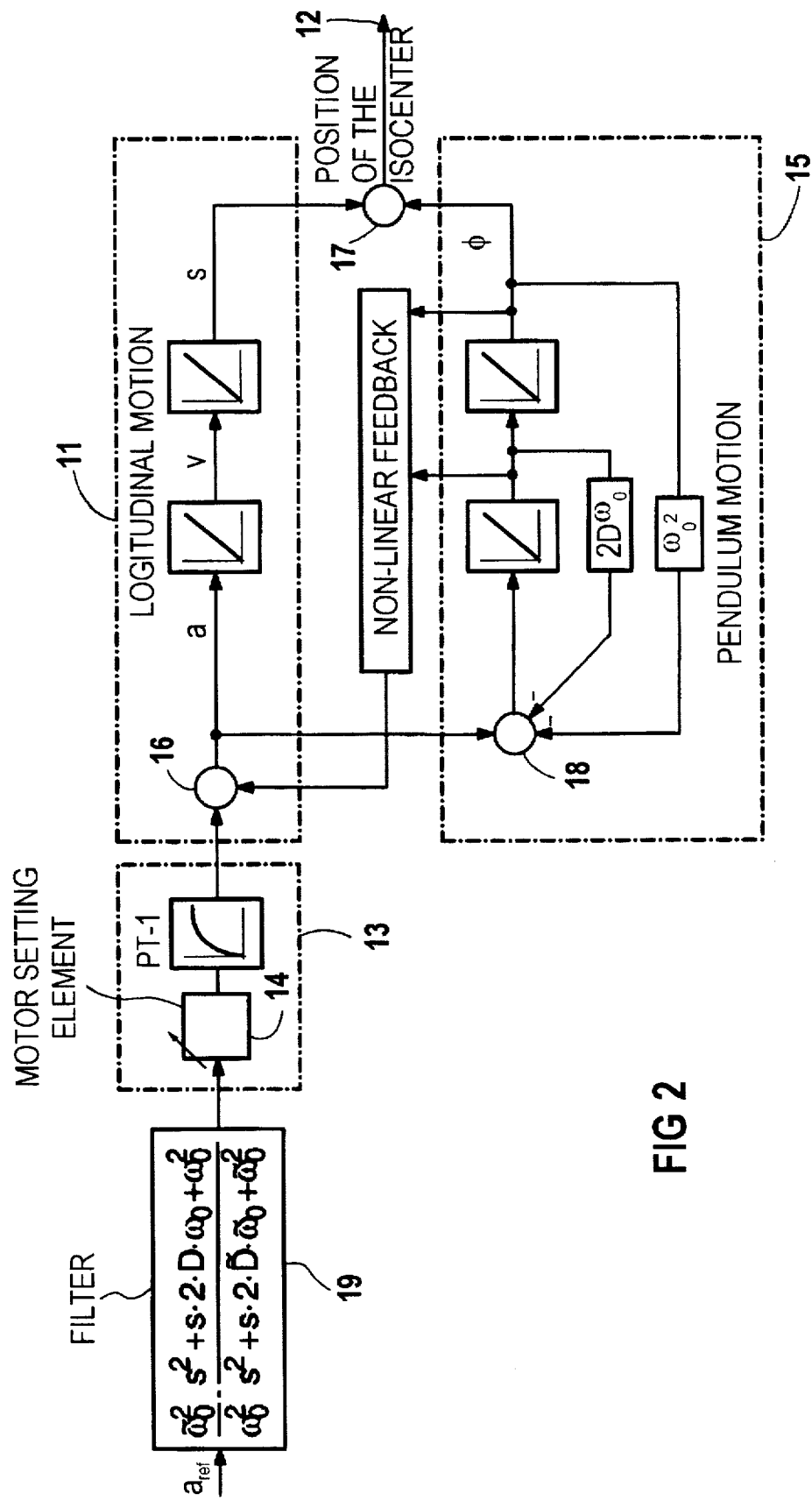
FIG. 2 shows a schematic representation of a motion control circuit for the X-ray apparatus in FIG. 1, according to the invention.

In FIG. 2, an isocenter position modeling stage 11 electronically models (mimics) the effect of the quantities a, v and s on the position of the isocenter of the C-arm 1, which is expressed at the output 12. The quantities a, v and s of the longitudinal motion act in linear fashion, which is expressed by the two blocks in the stage 11. A drive motor stage 13 represents the drive motor (not shown in FIG. 1) for the longitudinal motion corresponding to the double arrow 8; this is the motor motion corresponding to the curved diagram block contained therein. The stage 13 additionally contains a setting element 14 for the longitudinal motion.

The pendulum motion is modeled by the components in a pendulum modeling stage 15. In the stage 15, the designation D thereby signifies the diameter of the C-arm 1, and $\omega_0$ signifies the basic angular velocity thereof. The pendulum motion is superimposed on the linear motion, as modeled by the superposition in the summation elements 16, 17 and 18.

If the pendulum motion is avoided, the apparatus, and thus its isocenter as well, can be operated without oscillation, eliminating waiting periods for the user. For the avoidance of this pendulum motion, a filter 19 is connected in front of the setting element 14 for the motor 13. This filter 19 can be of analog or digital design. The characteristic system behavior is determined once, so that the oscillation behavior of the apparatus is known, this motion then being compensated by the filter 19, which gives the apparatus motion a predeterminable dynamic motion component which compensates the pendulum motion. The quantities having a tilde in the filter 19 are the quantities that would arise during oscillation.

The apparatus reacts entirely without pendulum motion to a discontinuous change in the acceleration target value a.

Although modifications and changes may be suggested by those skilled in the art, it is the intention of the inventor to embody within the patent warranted hereon all changes and modifications as reasonably and properly come within the scope of their contribution to the art.

I claim as my invention:

1. An x-ray apparatus comprising:

a plurality of x-ray diagnostic components;

suspension means for suspending said plurality of x-ray diagnostic components from a ceiling, including a motor for moving said plurality of x-ray diagnostic components along the ceiling, said suspension means and said plurality of x-ray diagnostic components comprising a system which exhibits a system behavior including pendulum-like oscillations when moved; and a motor control circuit which emits control signals for operating said motor, including means for electronically modeling a longitudinal motion of said system along the ceiling, means for electronically modeling said pendulum-like oscillations and superimposing the modeled pendulum-like oscillations on the longitudinal motion, and filter means for producing a selected compensating factor in an output signal of said motor control circuit for eliminating said pendulum-like oscillations, and a setting stage having an output signal which drives said motor, said setting stage being connected between said filter and said means for modeling said longitudinal motion.

2. An apparatus as claimed in claim 1 wherein said plurality of x-ray diagnostic components comprising:

a C-arm having first and second opposite ends and a circumference extending between said first and second ends;

an x-ray source attached at said first end of said C-arm;

an x-ray imaging system attached at said second end of said C-arm;

a C-arm mount connected to said C-arm for displacing and rotating said C-arm along said circumference;

a bow on which said C-arm mount is displaceably mounted, said bow being connected to said suspension means.

* * * * *